United States Patent [19]

Compton et al.

[11] 4,309,557

[45] Jan. 5, 1982

[54] PROCESS FOR THE PREPARATION OF ALKYL AND ARYL SUBSTITUTED OLIGOSILOXANES SUITABLE FOR USE AS DIFFUSION PUMP OILS

[75] Inventors: Richard A. Compton, Santa Barbara; Del J. Petraitis, Goleta, both of Calif.

[73] Assignee: NuSil Research, Carpinteria, Calif.

[21] Appl. No.: 234,027

[22] Filed: Feb. 12, 1981

[51] Int. Cl.$^3$ .............................. C07F 7/08; C07F 7/18
[52] U.S. Cl. .................................................. 556/453
[58] Field of Search ....................................... 556/453

[56] References Cited

U.S. PATENT DOCUMENTS

| | | | |
|---|---|---|---|
| 2,890,234 | 6/1959 | Fletcher et al. | 556/453 |
| 3,334,318 | 2/1967 | Brady | 556/453 X |
| 3,354,101 | 11/1967 | Williams et al. | 556/453 X |
| 3,523,131 | 8/1970 | Sliwinski | 556/453 |
| 3,792,071 | 2/1974 | Nitzsche et al. | 556/453 X |

FOREIGN PATENT DOCUMENTS

| | | | |
|---|---|---|---|
| 1888279 | 9/1959 | France | 556/453 |
| 787800 | 12/1957 | United Kingdom | 556/453 |
| 808613 | 2/1959 | United Kingdom | 556/453 |

OTHER PUBLICATIONS

Eabor, "Organosilicon Compounds", Butterworth Scientific Pub., London (1960), pp. 300-329.
Sprung et al., J. Am. Chem. Soc., 77, p. 4173 (1955).
Noll, "Chemistry and Technology of Silicones", Academic Press, N.Y. (1968), pp. 41-49.

*Primary Examiner*—Paul F. Shaver
*Attorney, Agent, or Firm*—Jackson, Jones & Price

[57] ABSTRACT

An improved process for preparing 1,3-dialkyl-1,1,3,3-tetraryldisiloxanes and 1,3,5-trialkyl-1,1,3,5,5-pentaaryltrisiloxanes is disclosed. The process utilizes an aryl Grignard reagent to affect displacement of alkoxy, preferably methoxy, groups in the corresponding alkylalkoxy substituted di-, and trisiloxanes. Alternatively, partial replacement of the alkoxy groups in an alkyltrialkoxysilane with aryl groups in a Grignard reaction, and subsequent hydrolyis of the remaining alkoxy groups yield the above-noted desired compounds.

56 Claims, No Drawings

PROCESS FOR THE PREPARATION OF ALKYL AND ARYL SUBSTITUTED OLIGOSILOXANES SUITABLE FOR USE AS DIFFUSION PUMP OILS

BACKGROUND OF THE INVENTION

1. Field of the Invention

The present invention is directed to an improved process for preparing alkyl and aryl substituted oligosiloxanes suitable for use as diffusion pump oils. More particularly, the present invention is directed to employing Grignard reactions for the preparation of 1,3,5-trimethyl, 1,1,3,5,5-pentaphenyltrisiloxane which is eminently suited for use as a diffusion pump oil.

2. Brief Description of the Prior Art

Organic liquids or oils have been in use for a long time as diffusion pump oils. In order to be suitable for use as a diffusion pump oil, an oil must have low volatility and yet be vacuum distillable. Perhaps even more importantly, the oil must have a very high degree of thermal stability.

It was recognized a long time ago in the prior art that certain organo-siloxane compounds readily meet the above-noted requirements and therefore are well suited for use as diffusion pump oils. More particularly, it was recognized in the prior art that certain methyl and phenyl substituted trisiloxanes serve well as diffusion pump oils. Still more particularly, British Pat. No. 787,800 describes the synthesis and use of 1,3,3,5-tetramethyl,-1,1,5,5-tetraphenyltrisiloxane as a diffusion pump oil. British Pat. No. 808,613 describes the preparation and use of 1,3,5-trimethyl,-1,1,3,5,5-pentaphenyltrisiloxane as a diffusion pump oil.

Although the application of the above-noted specific compounds as diffusion pump oils has been sustantially universally accepted in the art, the use of these compounds still suffers from the disadvantage of relatively high costs. The high costs are principally occasioned by the general inadequacy, and more particularly by the low yields of the state-of-the-art synthetic processes for preparing these compounds.

For example, 1,3,5-trimethyl,-1,1,3,5,5-pentaphenyltrisiloxane has hitherto been prepared by co-hydrolysis of the corresponding alkyl and aryl substituted chlorosilanes, by catalytic co-polymerization of tetraphenyl-dimethyldisiloxane and phenylmethylsiloxane, or by the reaction of the sodium salt of diphenylmethylsilanol with phenylmethyldichlorosilane. British Pat. No. 808,613 states that the "best" process for preparing 1,3,5-trimethyl,-1,1,3,5,5-pentaphenyltrisiloxane involves the reaction of diphenylmethylsilanol with phenylmethyldichlorosilane. As is stated in British Pat. No. 787,800, the "best" process for preparing 1,3,3,5-tetramethyl-1,1,5,5-tetraphenyltrisiloxane involves the reaction of diphenylmethylsilanol with dimethyldichlorosilane.

Because experience has shown that the above-noted two processes are relatively uneconomical due to their low yield and excessive side product formation, the principal object of the present invention was to provide an alternative synthetic route to alkyl and aryl substituted oligosiloxanes in general, and to 1,3,5-trimethyl,-1,1,3,5,5-pentaphenyltrisiloxane in particular. The desired synthetic route was expected to be more economical principally because of lesser degree of side product formation and hence better yields.

The present invention utilizes aryl Grignard reagents to replace alkoxy leaving groups either in already formed alkyl, alkoxy substituted oligosiloxanes or in alkyl-alkoxy substituted silane precursors of the desired oligosiloxanes. In order to properly illuminate the background chemistry of the present invention, attention is directed to the book "Chemistry and Technology of Silicones", written by Walter Noll, Academic Press, New York, San Francisco, London, 1968 and particularly to pages 41–49 thereof. The above-noted pages discuss the use of organometallic reagents, such as Grignard reagents in the chemistry of silicones. Other references of interest to the present invention are the following: "Organosilicon Compounds" by C. Eaborn, Butterworth Scientific Publications, 1960 (London), pages 307–312, and "The Partial Hydrolysis of Methyl-trimethoxysilane" by M. M. Sprung and F. O. Guenther, J. Am. Chem. Soc., 77, 4173 (1955).

SUMMARY OF THE INVENTION

It is an object of the present invention to provide a relatively economical synthetic process for the preparation of alkyl and aryl substituted oligosiloxanes, and particularly for the preparation of 1,3,5-trimethyl-1,1,3,5,5-pentaphenyltrisiloxane.

It is another object of the present invention to provide a synthetic process for the preparation of alkyl and aryl substituted oligosiloxanes wherein the formation of undesirable halogenated biphenyls is avoided.

In accordance with the present invention, an oligosiloxane or a silane containing alkyl and alkoxy substituents is reacted with an aryl Grignard reagent to provide, respectively, an oligosiloxane or silane having alkyl and aryl substituents.

According to one aspect of the present invention, a compound having the general formula of $Alkyl_1$—Si—$(OAlkyl_2)_3$ wherein $Alkyl_1$ has 1 or 2 carbons and $Alkyl_2$ has 1–6 carbons, is allowed to undergo partial hydrolysis and condensation to provide the oligosiloxane having alkyl and alkoxy substituents. The oligosiloxane is then reacted with the aryl Gignard reagent to replace all of its remaining alkoxy substituents with aryl groups.

In accordance with another aspect of the present invention, the compound $Alkyl_1$—Si—$(OAlkyl_2)_3$ is reacted with an aryl Gignard reagent in a manner so as not to replace all of the alkoxy substituents with the aryl group. The resulting alkyl-alkoxy-aryl-silanes are subjected to hydrolysis and substantially simultaneous condensation to give the desired alkyl-aryl-oligosiloxanes having no residual alkoxy groups. Trisiloxanes, and to a lesser extent disiloxanes, prepared in accordance with the present invention are useful as diffusion pump oils.

Further features and aspects of the present invention can be best understood from the ensuing detailed description and specific examples.

DETAILED DESCRIPTION OF THE INVENTION

The following description sets forth the preferred embodiments of the present invention in such a manner that any person skilled in the chemistry of silicon compounds can use the invention. The embodiments of the invention disclosed herein are the best modes contemplated by the inventors for carrying out their invention in a commercial environment, although it should be understood that various modifications can be accomplished within the parameters of the present invention.

The present invention is directed to the relatively economical preparation of compounds having the General Formula I which are useful as diffusion pump oils.

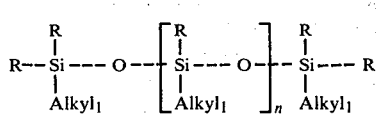

GENERAL FORMULA I wherein n equals 0 to 1, $Alkyl_1$ is an alkyl group having 1-2 carbons and R is an aryl or alkylaryl group, with the alklaryl group having 1 or 2 carbons in the alkyl chain.

As it was stated briefly in the introductory section of the present application for patent, a diffusion pump oil must have low volatility and yet be distillable in high vacuum. It also must have a very high degree of thermal stability. The limitations regarding the number of siloxane moieties, and the nature of the alkyl and aryl or alkylaryl side chains in the compounds corresponding to General Formula I are principally imposed by the above stated requirements.

Thus, it was found in practice that certain trisiloxanes (n=1) and to a somewhat lesser extent disiloxanes (n=0) have the requisite properties regarding volatility in order to serve as diffusion pump oils. Furthermore, only short alkyl substituents on the silicon atom and on the alkyl side chain of the alkylaryl group have sufficient thermal stability to withstand gradual degradation, under the high temperatures of an operating vacuum diffusion pump. Therefore, the presence of the aryl or alkylaryl substituents in the compounds of General Formula I is required to confer the requisite low volatility, while the aryl or alkylaryl groups, particularly mononuclear aryl groups such as the phenyl group, possess the requisite thermal stability.

Most preferred compounds which are prepared in accordance with the present invention are in decreasing order of preference:

1,3,5-trimethyl, 1,1,3,5,5-pentaphenyltrisiloxane (Formula II); 1,3,3,5-tetramethyl, 1,1,5,5-tetraphenyltrisiloxane (Formula III), and 1,3, dimethyl, 1,1,3,3-tetraphenyldisiloxane (Formula IV).

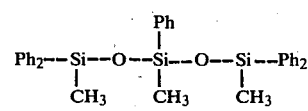

FORMULA II

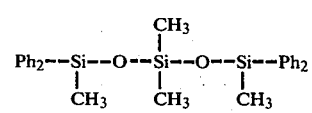

FORMULA III

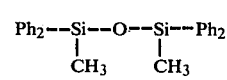

FORMULA IV

According to the process of the present invention, the compounds of General Formula I are prepared by the use of a Grignard reagent which is characterized in General Formula V, R—Mg—X   GENERAL FORMULA V wherein X is Cl, Br or I and R is as defined as above for General Formula I. The Grignard reaction with the reagent R—Mg—X is preferably performed in tetrahydrofurane, although other solvents conventionally used for carrying out Grignard reactions may also be used. It was found desirable in some instances to add xylene or like high boiling inert solvent to the medium wherein the Grignard reaction is conducted in order to raise the reaction temperature.

According to one aspect of the novel process of the present invention, the Grignard reaction is performed on a compound having the General Formula VI in such a manner that not all of the alkoxy substituents of the compound are replaced by the R group of the Grignard reagent.

$Alkyl_1$—Si—$(OAlkyl_2)_3$   GENERAL FORMULA VI

In the compounds of General Formula VI, $Alkyl_1$ is defined as above, and $Alkyl_2$ is an alkyl group having 1-6 carbons.

In order to eventually obtain trisiloxanes of the type set forth in General Formula I, it is necessary to obtain in the Grignard reaction of R—Mg—X with $Alkyl_1$—Si—$(OAlkyl_2)_3$ monoaryl and diaryl substituted alkyl-alkoxysilanes which respectively correspond to a General Formulae VII and VIII.

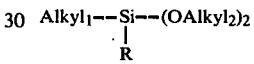

GENERAL FORMULA VII

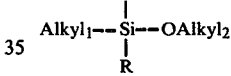

GENERAL FORMULA VIII

Generally speaking, both the desired monoaryl and diaryl substituted alkylalkoxysilanes are formed in the Grignard reaction, although usually some undesired triarylalkylsilane is also formed. The ratio of the several products in this Grignard reaction is influenced to some extent by the molar ratio of the Grignard reagent to the alkyltrialkoxysilane. For example when $CH_3$—Si—$(OCH_3)_3$ is used, phenyl magnesium bromide is employed in a 1.5 to 1.75 molar ratio relative to $CH_3$—Si—$(OCH_3)_3$.

The monoaryl and diaryl substituted alkyl-alkoxysilanes, the compounds of General Formulae VII and VIII, are usually separable from one another and from other contaminants by fractional distillation and/or fractional vacuum distillation. In some cases it is, however, advantageous to employ fractional distillation, and/or vacuum distillation merely to remove some of the more volatile monoaryl-alkylalkoxysilane (compound of General Formula VII), so as to adjust in the remaining mixture the molar ratio of the monoaryl-alkyl-dialkoxysilane (General Formula VII) to diaryl-alkylalkoxysilane (General Formula VIII) to approximately 1:2.

In accordance with one preferred embodiment and specific example of the process of the present invention wherein $CH_3$—Si—$(OCH_3)_3$ is reacted with phenyl magnesium bromide, methylphenyldimethoxysilane is formed in excess of its desired ratio. The excess is removed by distillation so that the remaining intermediate product mixture is adjusted to have an approximate ratio of methyl-phenyldimethoxysilane to methyldiphenylmethoxysilane of 1.2:2. The removed excess of methyl-phenyldimethoxysilane may be added to the Grignard reaction wherein $CH_3$—Si—$(OCH_3)_3$ is reacted with phenyl magnesium bromide to increase the yield of the desired methyl-diphenylmethoxysilane.

In the next step of the process of the present invention as it is practiced in accordance with the first aspect thereof, the compounds of the General Formulae VII and VIII (present preferably in approximately 1:2 molar ratios) are heated with strong aqueous mineral base to affect hydrolysis of the remaining alkoxy groups. Substantially simultaneous condensation of the siloxane moieties yields a product mixture containing the desired compounds in accordance with General Formula I. Potassium hydroxide is well suited as the strong mineral base for affecting the hydrolysis and condensation.

Although the product mixture of the hydrolysis and condensation reaction contains other components such as cyclic tri-, and higher siloxanes as well as linear tetra-, and higher siloxanes, the desired products may be readily isolated by fractional vacuum distillation. In accordance with established procedures in the prior art, the cyclic and linear siloxane side products may be treated with strong mineral base such as KOH to cause equilibration and formation of more of the desired products corresponding to General Formula I.

In accordance with another aspect of the present invention, the alkyl-trialkoxysilane compounds of General Formula VI are partially hydrolyzed and simultaneously condensed to give intermediate alkyl-alkoxyoligosiloxanes, compounds corresponding to General Formula IX, wherein the symbols Alkyl$_1$, Alkyl$_2$ and n have the same meaning as above.

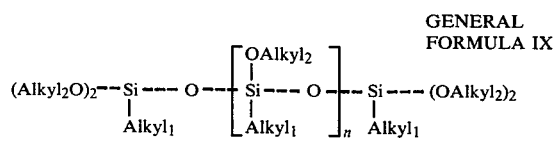

GENERAL FORMULA IX

The partial hydrolysis and condensation step is carried out in analogy to the procedure described in the reference article, J. Am. Chem. Soc. 77, 4173 (1955). It is affected by heat in the presence of strong and weak aqueous mineral bases, strong and weak acids and acid anhydrides. In essence, ⅔ molar ratio is required to yield from the alkyltrialkoxysilane a trisiloxane compound corresponding to General Formula IX, wherein n=1.

In practical experience it was found that optimum results are obtained when the hydrolysis reaction is not allowed to consume all of the starting alkyltrialkoxysilane compound. Instead the hydrolysis reaction is interrupted at an earlier stage. For reasons of economy, the unreacted alkyltrialkoxysilane is recovered from the reaction mixture. Products of the hydrolysis and condensation reaction include the desired intermediate di-, and trisiloxanes corresponding to the General Formula IX, as well as undesired cyclic tri-, and higher siloxanes, and linear tetra-, and higher siloxanes.

The desired intermediate alkyl-alkoxydisiloxanes and alkyl-alkoxy-trisiloxanes may be respectively isolated in substantially pure states by distillation in vacuum. In practice however, it is sufficient to obtain a fraction which contains the desired alkyl-alkoxydisiloxanes and alkyl-alkoxytrisiloxanes substantially free of starting alkyl-trialkoxysilane and methanol.

In the next step of the process of the present invention as practiced in accordance with the herein described second aspect thereof, the compounds of General Formula IX are reacted with a Grignard reagent R—Mg—X to yield the desired products corresponding to the General Formula I.

As it was mentioned hereinbefore, the Grignard reaction is preferably performed in hot THF, containing some xylene. The Grignard reaction of the compounds of the General Formula IX forms substantially no undesirable side products, and gives a substantially 100% yield. The final products are readily obtained in substantially pure state from the Grignard reaction by fractional vacuum distillation.

In accordance with a third aspect of the process of the present invention, 1,3,3,5-tetraalkyl-1,1,5,5-tetraalkoxytrisiloxanes, the compounds corresponding to General Formula X wherein Alkyl$_1$ and Alkyl$_2$ are defined as above, and Z is an alkyl group of 1–2 carbons, are reacted with the Grignard reagent R—Mg—X to give, in excellent yields, 1,3,3,5-tetraalkyl-1,1,5,5-tetraaryltrisiloxanes. The letter compounds are represented by General Formula XI wherein Y has the same definition as Z above.

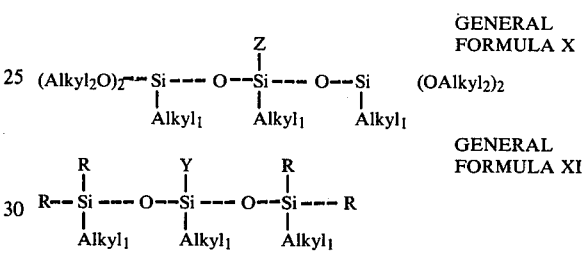

As an example, 1,3,3,5-tetramethyl-1,1,5,5-tetraphenyltrisiloxane (Formula III) is obtained in this manner from 1,3,3,5-tetramethyl-1,1,5,5-tetramethoxytrisiloxane with the use of phenyl magnesium bromide. The starting material 1,3,3,5-tetramethyl-1,1,5,5 tetramethoxytrisiloxane may be obtained in accordance with the teachings of the prior art by reaction of dimethoxymethylsilanol with dimethyldicholorosilane.

Generally speaking, the use of phenyl magnesium bromide as the Grignard reagent, methoxy group as the alkoxy substituents, and methyl group as the alkyl substituents is preferred in the several embodiments of the process of the present invention.

Important advantages of the process of the present invention are improved yields and relatively low degree of side product formation as compared to the prior art. Another advantage of replacing alkoxy rather than halo groups in a Grignard reaction is the complete avoidance of the formation of halogenated biphenyls.

The following specific examples further illustrate the novel process of the present invention. It should be specifically understood that the specific parameters of the specific examples are for the purpose of fully disclosing the present invention, and not for the purpose of limiting the same. Accordingly, the scope of the present invention should be limited only by the appended claims.

EXAMPLE I.

Partial Hydrolysis of $CH_3$—Si—$(OCH_3)_3$ to Linear Oligosiloxanes.

$CH_3$—Si—$(OCH_3)_3$ and $H_2O$ containing 1.25 g/l NaOH are continuously added to an agitated 5 L reaction vessel at a ratio of one mole $CH_3$—Si—$(OCH_3)_3$ to 0.44 moles of $H_2O$. The combined rate of addition of $CH_3$—Si—$(OCH_3)_3$ and $H_2O$ is approximately 0.5 liters/minute. The reaction vessel is heated so as to maintain an internal temperature of approximately 65° C. The contents of the reaction vessel comprising the product of hydrolysis are allowed to exit by overflow into a storage container.

The hydrolyzate is subjected to distillation to remove methanol and unreacted $CH_3$—Si—$(OCH_3)_3$ (b.p 103° C. at 760 Hgmm) which is recovered in approximately 35% yield.

The remainder of the hydrolyzate is subjected to vacuum distillation to isolate 1,1,3,5-tetramethoxy-1,3,-dimethyldisiloxane (b.p 44.5° C./3 mm) and 1,1,3,5,5-pentamethoxy-1,3,5-trimethyltrisiloxane (b.p 94° C./5 mm) either in respectively pure states or as a mixture with one another. From 100 parts by weight of starting $CH_3$—Si—$(OCH_3)_3$ approximately 10 parts of 1,1,3,5,5-pentamethoxy-1,3,5-trimethyl-trisiloxane and 20 parts of 1,1,3,3-tetramethoxy-1,1,-dimethyldisiloxane is obtained. The hydrolysis reaction also yields approximately 4 parts of the corresponding linear tetrasiloxane, and 2 parts of the corresponding linear pentasiloxane as well as other side products. Traces of sn, Pb and Fe ions interfere with the hydrolysis reaction. Therefore, special care must be taken to avoid these impurities. The reaction is best conducted in a glass vessel.

EXAMPLE II

Preparation of
1,3,5-Trimethyl-1,1,3,5,5-pentaphenyltrisiloxane by Grignard Reaction from
1,3,5-Trimethyl-1,1,3,5,5-pentamethoxytrisiloxane Into a 100 gallon capacity reaction vessel suitable for running a Grignard reaction, 12.8 kg of dry magnesium chips are added, followed by addition of 28 kg of dry THF. Subsequently, 4 kg of dry bromobenzene are added. After the formation of the Grignard reagent has initiated as evidenced by significant rise in temperature, simultaneous addition of additional bromobenzene and THF-xylene mixture (in the ratio of THF:xylene 1.0:1.3) is commenced. The bromobenzene is added at the rate of approximately 1.2 kg/min. and the THF-xylene is added at the rate of 3.0 kg/min. Cooling of the reaction vessel, and if necessary, the rate of addition of bromobenzene, are adjusted so as to maintain an internal temperature between 65°-140° C. The addition of THF-xylene is discontinued when a total of approximately 155 kg of the mixture has been added. When approximately 40.8 kg of bromobenzene has been added, addition of 1,3,5-trimethyl-1,1,3,5,5-trimethoxytrisiloxane is commenced at a rate of 0.8 kg/min. Alternatively, a mixture of 1,3,5-trimethyl-1,1,3,5,5-trimethoxytrisiloxane and 1,3-dimethyl-1,1,3,3-tetramethoxydisiloxane may be added at the same rate. A total of 19.0 kg of the above-noted trisiloxane or mixed trisiloxane and disiloxane are added in this manner. During the addition of the siloxanes, the addition of bromobenzene is continued until a total of 81.6 kg of bromobenzene has been added. After the addition of bromobenzene is completed, heating is applied to the reaction vessel as necessary to maintain an internal temperature of approximately 94° C. for approximately 1½ hours. After heating for 1½ hours, cooling is applied and 33 kg of $H_2O$ is added. An aqueous (lower) and an organic (upper) phase separates. The organic phase contains THF, xylene and product. The THF, xylene and any residual bromobenzene are removed from the upper phase by strip distillation. The residue is subjected to fractional vacuum distillation to obtain 1,3,5-trimethyl-1,1,3,5,5-pentaphenyltrisiloxane (b.p 245° C. at 0.5 Hgmm), and, if applicable, 1,3,-dimethyl-1,1,3,3-tetraphenyldisiloxane (b.p. 187° C. at approximately 0.5 Hgmm). The yield of the methylphenyl siloxanes is 95% or higher, based on the added methylmethoxy siloxanes.

EXAMPLE III

Preparation of
1,3,5-Trimethyl-1,1,3,5,5-pentaphenyltrisiloxane and 1,3-Dimethyl-1,1,3,3-tetraphenyldisiloxane via Methyldiphenylmethoxysilane and Methylphenyldimethoxysilane.

12.4 kg of dry magnesium chips are added, into a 100 gallon capacity reaction vessel suitable for running a Grignard reaction, followed by 28 kg of THF and 4 kg of bromobenzene. When formation of the Grignard reagent has commenced, $CH_3$—Si—$(OCH_3)_3$ and additional bromobenzene are added simultaneously at the respective rates of 1.1 Kg/min. and 0.7 kg/min. $CH_3$—Si—$(OCH_3)_3$ is always maintained at a molar excess relative to bromobenzene in order to avoid formation of undesirable biphenyl. After a total of 42 kg of $CH_3$—Si—$(OCH_3)_3$ and a total of 78.3 kg of bromobenzene are added, heat is applied as necessary in order to maintain an internal temperature of approximately 94° C. for approximately 2 hours. Thereafter the reaction mixture is cooled, and 33 kg of $H_2O$ is added to form two phase. The upper organic phase contains THF, methylphenyldimethoxysilane, methyldiphenylmethoxysilane, and some methyltriphenylsilane. The organic phase is strip distilled to remove THF, and the residue is subjected to fractional distillation. In the fractional distillation methylphenyldimethoxysilane (b.p. 199° C. at 750 Hgmm) and methyldiphenylmethoxysilane (b.p. 150° C. at 5 Hgmm) may be obtained in substantially pure states. These compounds are typically formed in approximately 1:1 ratio in the reaction. Alternatively and preferably, methylphenyldimethoxysilane is distilled out until the molar ratio of methyldiphenylmethoxysilane and methylphenyldimethoxysilane is adjusted in the residue to approximately 2.0:1.2. The concentration of these compounds is readily monitored by gas chromatography. In a typical reaction, from 100 parts by weight of $CH_3$—Si—$(OCH_3)_3$ 35 parts of methylphenyldimethoxysilane, and 51 parts of methyldiphenylmethoxysilane and 6 parts of methyltriphenylsilane are obtained.

A mixture of methyldiphenylmethoxysilane and methylphenyldimethoxysilane in the approximate molar ratio of 2.0:1.2 is refluxed with $H_2O$ and KOH for one hour. 10 moles of $H_2O$ and 0.08 moles of KOH are present for each 2 moles of methyldiphenylmethoxysilane. After reflux, the $H_2O$ and $CH_3OH$ which is formed in the reaction is distilled and trapped in a Dean-Stark-type trap, and the temperature is raised to 200° C. for one hour. Thereafter, 1,3,5-trimethyl-1,1,3,5,5-pentaphenyltrisiloxane and 1,3-dimethyl-1,1,3,3-tetraphenyldisiloxane are obtained by fractional vacuum distillation. In a typical reaction, from 100 parts by weight of mixed methyldiphenylmethoxysilane and methylphenyldimethoxysilane 15 parts of 1,3,5-trimethyl-1,1,3,5,5-pentaphenyltrisiloxane and 10 parts of 1,3,-dimethyl-1,1,3,3-tetraphenyldisiloxane are obtained.

What is claimed is:

1. A process for preparing compounds of the general formula:

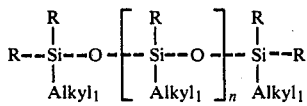

wherein
n equals 0 or 1,
Alkyl$_1$ is an alkyl group having 1-2 carbons and R is an aryl, or alkylaryl group said alkylaryl group having 1-2 carbons in the alkyl chain,
the process comprising the steps of:
reacting a compound of the general formula of

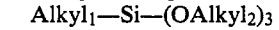

wherein Alkyl$_1$ is defined as above and Alkyl$_2$ is an alkyl group having 1-6 carbon atoms, with a Grignard reagent derived from a compound having the general formula of R—X, wherein R is defined as above and X is Cl, Br or I, said reaction with the Grignard reagent giving rise to a mixture containing the compounds of the following two general formulae:

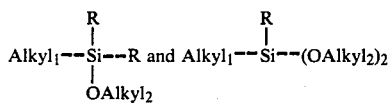

wherein Alkyl$_1$, Alkyl$_2$ and R have the same definition as above;
subjecting a mixture containing at least the compounds of the two general formulae:

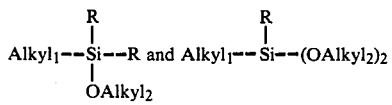

to hydrolysis to remove the OAlkyl$_2$ groups, and substantially simultaneously with said hydrolysis allowing condensation of the respective siloxanes moieties to occur.

2. The process of claim 1 wherein n is 0.
3. The process of claim 2 wherein Alkyl$_1$ is CH$_3$, and R is phenyl.
4. The process of claim 3 wherein Alkyl$_2$ is CH$_3$.
5. The process of claim 1 wherein n is 1.
6. The process of claim 5 wherein Alkyl$_1$ is CH$_3$.
7. The process of claim 5 wherein Alkyl$_2$ is CH$_3$.
8. The process of claim 5 wherein Alkyl$_1$ is CH$_3$ and Alkyl$_2$ is CH$_3$.
9. The process of claim 5 wherein R is phenyl.
10. The process of claim 5 wherein Alkyl$_1$ is CH$_3$, Alkyl$_2$ is CH$_3$ and R is phenyl.
11. The process of claim 10 wherein X is Br.
12. The process of claim 10 wherein in the reacting step the molar ratio of CH$_3$—Si—(OCH$_3$)$_3$ PhX is approximately 1:1.5-1.75.
13. The process of claim 12 additionally comprising the step of isolating by fractional distillation after the reacting step a fraction essentially consisting of compounds selected from a class consisting of methylmethoxydiphenylsilane and methyldimethoxyphenylsilane.
14. The process of claim 12 further comprising the step of isolating after the reacting step a fraction essentially consisting of methyl-dimethoxyphenysilane.

15. The process of claim 15 wherein in the reacting step said methyl-dimethoxyphenylsilane is added to the reaction mixture to increase the yield of methylmethoxydiphenylsilane.
16. The process of claim 13 further comprising the step of adjusting by fractional distillation prior to said hydrolysing step the molar ratio of methyl-methoxydiphenylsilane and methyl-dimethoxyphenysilane to approximately 2:1.2.
17. The process of claim 16 wherein the hydrolysis step is performed with aqueous alkali metal or alkali earth metal hydroxide solution.
18. The process of claim 17 wherein the step of hydrolysis is performed with aqueous potassium hydroxide solution.
19. The process of claim 1 wherein the step of hydrolysis is performed with aqueous alkali metal or alkali earth metal hydroxide solution.
20. The process of claim 19 wherein the step of hydrolysis is performed with aqueous potassium hydroxide solution.
21. A process for preparing compounds of the general formula

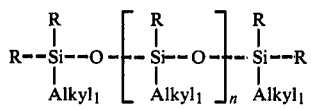

wherein
n equals 0 or 1, and
Alkyl$_1$ is an alkyl group having 1-2 carbons, and R is an aryl or alkylaryl group, said alkylaryl group having 1-2 carbons in the alkyl chain,
the process comprising the steps of:
hydrolysing and substantially simultaneously condensing a compound of the general formula of

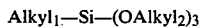

wherein Alkyl$_1$ is defined as above and Alkyl$_2$ is an alkyl group having 1-6 carbons, to yield linear oligosiloxanes of the general formula

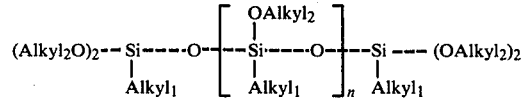

wherein
n equals 0 or 1, and
Alkyl$_1$ and Alkyl$_2$ are defined as above, and
reacting at least one of the linear oligosiloxanes of the above defined general formula with a Grignard reagent derived from a compound having the general formual of R-X wherein R is defined as above and X is Cl, Br or I.

22. The process of claim 21 wherein n equals 0.
23. The process of claim 22 wherein Alkyl$_1$ is CH$_3$.
24. The process of claim 22 wherein Alkyl$_2$ is CH$_3$.
25. The process of claim 22 wherein Alkyl$_1$ is CH$_3$ and Alkyl$_2$ is CH$_3$.
26. The process of claim 22 wherein R is phenyl.
27. The process of claim 22 wherein Alkyl$_1$ is CH$_3$, Alkyl$_2$ is CH$_3$ and R is phenyl.
28. The process of claim 27 wherein X is Br.

29. The process of claim 21 wherein n equals 1.
30. The process of claim 29 wherein Alkyl$_1$ is CH$_3$.
31. The process of claim 29 wherein Alkyl$_2$ is CH$_3$.
32. The process of claim 29 wherein Alkyl$_1$ and Alkyl$_2$ are CH$_3$.
33. The process of claim 29 wherein R is phenyl.
34. The process of claim 29 wherein Alkyl$_1$ is CH$_3$ and R is phenyl.
35. The process of claim 34 wherein Alkyl$_2$ is CH$_3$.
36. The process of claim 35 wherein X is Br.
37. The process of claim 35 further comprising the step of separating prior to the reacting step a mixture comprising 1,3-dimethyl, 1,1,3,3-tetramethoxydisiloxane, and 1,3,5 trimethyl, 1,1,3,5,5-pentamethoxytrisiloxane from unreacted methyltrimethoxysilane and methanol.
38. The process of claim 37 further comprising the step of isolating prior to said reacting step substantially pure 1,3,5-trimethyl, 1,1,3,5,5-pentamethoxytrisiloxane from said mixture.
39. The process of claim 37 wherein the step of hydrolysing is conducted with aqueous sodium hydroxide solution.
40. The process of claim 21 wherein the step of hydrolysing is conducted with aqueous sodium hydroxide solution.
41. A process for preparing a 1,3,5 trimethyl-1,1,3,5,5 pentaphenyltrisiloxane, said process comprising the steps of:
hydrolysing and substantially simultaneously condensing a compound having the general formula of CH$_3$—Si—(OAlkyl$_2$)$_3$, wherein Alkyl$_2$ is an alkyl group having 1–6 carbons, with water in the presence of a catalyst selected from a group consisting of strong bases, strong acids, weak acids and acid anhydrides;
isolating from the medium of said hydrolysis and condensation and in a state substantially free of methanol and unreacted CH$_3$—Si—(OAlkyl$_2$)$_3$) a mixture comprising 1,3,5-trimethyl-1,1,3,5,5-pentaalkoxytrisiloxane and 1,3-trimethyl, 1,1,3,3 tetraalkoxydisiloxane;
reacting said 1,3,5-trimethyl-1,1,3,5,5-pentaalkoxytrisiloxane with a Grignard reagent derived from Ph-X, wherein X is Cl, Br or I, and
isolating by fractional distillation from the products of said Grignard reaction 1,3,5-trimethyl-1,1,3,5,5-pentaphenyltrisiloxane.
42. The process of claim 41 wherein Alkyl$_2$ is CH$_3$.
43. The process of claim 42 wherein the catalyst is sodium hydroxide.
44. The process of claim 42 wherein X is Br.
45. The process of claim 41 wherein Alkyl$_2$ is CH$_3$ and wherein the process additionally comprises the step of separating by distillation 1,3, dimethyl-1,1,3,3-tetramethoxydisiloxane from said mixture.
46. A process for preparing compounds having the general formula of

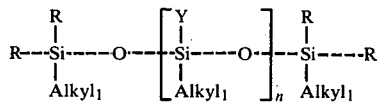

wherein
n is 0 or 1,
Alkyl$_1$ is an alkyl group having 1–2 carbons and
R is an aryl, or alkylaryl group, said alkylaryl group having 1–2 carbons in the alkyl chain, and
Y is the same as R, or is an alkyl group having 1–2 carbons, the process comprising the step of:
reacting with a Grignard reagent derived from R-X wherein X is Cl, Br or I and R is defined as above, compounds having the general formula of

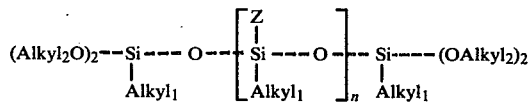

wherein n and Alkyl$_1$ are defined as above,
Alkyl$_2$ is an alkyl group having 1–6 carbons, and
Z is an alkoxy group having 1–6 carbons or is an alkyl group having 1–2 carbons, with the further restriction that when Z is an alkyl group then Y is the same as Z.
47. The process of claim 46 wherein Alkyl$_1$ is CH$_3$.
48. The process of claim 46 wherein Alkyl$_2$ is CH$_3$.
49. The process of claim 46 wherein Alkyl$_1$ and Alkyl$_2$ are CH$_3$.
50. The process of claim 46 wherein R is phenyl.
51. The process of claim 46 wherein n is 1, R is phenyl and Alkyl$_1$ is CH$_3$.
52. The process of claim 46 wherein n is 1, R is phenyl, Y is phenyl, Z is OCH$_3$, and Alkyl$_2$ is CH$_3$.
53. The process of claim 52 wherein X is Br.
54. The process of claim 46 wherein n is 1, Z is CH$_3$, Y is CH$_3$ Alkyl$_1$ is CH$_3$, and R is phenyl.
55. The process of claim 54 wherein Alkyl$_2$ is CH$_3$.
56. The process of claim 55 wherein X is Br.

* * * * *